United States Patent
Schellenberger

(12) 
(10) Patent No.: US 6,248,541 B1
(45) Date of Patent: Jun. 19, 2001

(54) SCREENING UNDER NUTRIENT LIMITED CONDITIONS

(75) Inventor: Volker Schellenberger, Palo Alto, CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/556,921

(22) Filed: Apr. 21, 2000

(51) Int. Cl.$^7$ .............................. C12Q 1/02; C12Q 3/00; C12Q 1/25; C12N 5/02

(52) U.S. Cl. .......................... 435/7.1; 435/7.2; 435/7.21; 435/325; 435/243; 435/252.3; 435/376; 435/29; 435/30; 435/34; 435/375; 435/7.4

(58) Field of Search .................................. 435/6, 7.1, 7.2, 435/7.21, 325, 243, 252.3, 376, 29, 30, 34, 375, 7.4

(56) References Cited

U.S. PATENT DOCUMENTS

| | | |
|---|---|---|
| 5,093,257 | 3/1992 | Gray . |
| 5,270,170 | 12/1993 | Schatz et al. . |
| 5,521,077 | 5/1996 | Khosla et al. . |
| 5,830,696 | 11/1998 | Short . |

FOREIGN PATENT DOCUMENTS

| | | |
|---|---|---|
| 0 563 103 B1 | 12/1991 | (EP) . |
| WO 87/01374 | 3/1987 | (WO) . |
| WO 97/07205 | 2/1997 | (WO) . |
| WO 97/15657 | 5/1997 | (WO) . |
| WO 97/46670 | 12/1997 | (WO) . |
| WO 98/05765 | 2/1998 | (WO) . |
| WO 98/10102 | 3/1998 | (WO) . |
| WO 98/17684 | 4/1998 | (WO) . |
| WO 98/28416 | 7/1998 | (WO) . |
| WO 98/41622 | 9/1998 | (WO) . |
| WO 98/41623 | 9/1998 | (WO) . |
| WO 98/41653 | 9/1998 | (WO) . |
| WO 98/51802 | 11/1998 | (WO) . |

OTHER PUBLICATIONS

Bashkirov, V., et al., "Interplasmidic illegitimate recombination in *Bacillus subtilis*," *Mol Gen Genet*, V.1, 213 pp. 465–470 (1988).

Berger, S. et al, "Phoenix Mutagenesis: One–Step Reassembly of Multiply Cleaved Plasmids with Mixtures of Mutant and Wild–Type Fragments," *Analytical Biochemistry*, 214, pp. 571–579 (1993).

Byron, S. et al, "Ultraviolet Inactivation and Excision–Repair in *Bacillus subtilis*," *Mutation Research*, 15 pp. 1–10 (1972).

Canosi, U. et al, "Plasmid Transformation in *Bacillus subtilis*: Effects of Insertion of *Bacillus subtilis* DNA into Plasmid pC194," *Mol Gen Genet*, 181, pp. 434–440 (1981).

Cheng, S. et al, "Effective amplification of long targets from cloned inserts and human geonomic DNA," *Proc. Natl. Acad. Sci. USA*, V.91, pp. 5695–5699 (1994).

Contente, S. et al, "Marker Rescue Transformation by Linear Plasmid DNA in *Bacillus subtilis*, " *Plasmid*, 2, pp. 555–571 (1979).

Crameri, A. et al, "DNA shuffling of a family of genes from diverse species accelerates directed evolution," *Nature*, V.391 pp. 288–291 (1998).

Dustin, M. et al, "A novel Mutagenesis Stategy Identifies Distantly Spaced Amino Acid Sequences the are Required for the Phosphorylation of Both the Oligosaccharides of Procathepsin D by N–Acetylglucosamine 1–Phosphotransferase," *The Journal of Biological Chemistry*, V.270, No. 1, pp. 170–179 (1995).

Guerout–Fleury, A. et al, "Plasmids for ectopic integration in *Bacillus subtilis*," *Gene*, 180, pp. 57–61 (1996).

Hall, Berry G., "Changes in the substrate specificities of an Enzyme during Directed Evolution of New Functions," *Biochemistry*, 20, pp. 4042–4049 (1981).

Horton, R. M. et al, "Engineering hybrid genes without the use of restriction enymes: gene splicing by overlap extension," *Gene*, 77, pp. 61–68 (1989).

Iglesias, A. et al, "Plasmid Transformation in *Bacillus subtilis*: Symmetry of gene conversion in Transformation with a Hybrid Plasmid Containing Chromosomal DNA," *Mol Gen Genet*, 189, pp. 73–76 (1983).

Jansen, R. et al, "Disruption of phase during PCR amplification and cloning of heterozygous target sequences," *Nucleic Acids Research*, V.18, No. 17 pp. 5153–5156 (1990).

Judo, M. et al, "Stimulation and suppression of PCR–mediated recombination," *Nucleic Acids Research*, vol. 26, No. 7, pp. 1819–1825 (1998).

Kuchner, O. et al, "Directed evolution of enzyme catalysts," *TIB Tech*, vol. 15, 9 pages (1997).

Marton, A. et al, "DNA nicking favors PCR recombination," *Nucleic Acids Research*, vol. 19, No. 9, pp. 2423–2426 (1991).

Meyerhans, A. et al, "DNA recombination during PCR," *Nucleic Acids Research*, vol. 18, No. 7, pp. 1687–1691 (1990).

Michel, B. et al, "Intramolecular recombination during plasmid transformation of *Bacillus subtilis* competent cells," *The EMBO Journal*, vol. 1, No. 12, pp. 1565–1571 (1982).

Michel, B. et al, "Intermolecular recombination during Transformation of *Bacillus subtilis* Competent Cells by Monomeric and Dimeric Plasmids," *Plasmid*, 10, pp. 1–10 (1983).

(List continued on next page.)

Primary Examiner—David Guzo
(74) Attorney, Agent, or Firm—Christopher L. Stone

(57) ABSTRACT

Described herein are methods for obtaining from an initial population of cells a plurality of subpopulations of cells having a similar density by growing samples from the initial population in medium having a limiting nutrient. Also provided are methods for using such subpopulation of cells to identify members of an initial population, either spontaneously occurring or induced by mutagenesis, having altered and/or preferred phenotypes.

55 Claims, No Drawings

OTHER PUBLICATIONS

Ness, J. et al, "DNA shuffling of subgenomic sequences of subtilisin," *Nature Biotechnology*, vol. 17, pp. 893–896 (1999).

Niaudet, B. et al, "Insertional mutagensis in *Bacillus subtilis*: mechanism and use in gene cloning," *Gene*, 19, pp. 277–284 (1982).

Noirot, M.–A. et al, "Plasmid Replication Stimulates DNA Recombination in *Bacillus subtilis*," *J. Mol Biol.*, 196, pp. 39–48 (1987).

Odelberg, S. et al, "Template–switching during DNA synthesis by *Thermus aquaticus* DNA polymerase 1," *Nucleic Acids Research*, vol. 23, No. 11, pp. 2049–2057 (1995).

Paabo, S. et al, "DNA Damage Promotes Jumping between Templates during Enzymatic Amplification," *The Journal of Biological Chemistry*, vol. 265, No. 8, pp. 4718–4727 (1990).

Peck, Joel R., "A Ruby in the Rubbish: Beneficial Mutations, Deleterious Mutations and the Evolution of Sex," *Genetics*, 137, pp. 597–606 (1994).

Rudolph, C. et al, "Transformation of *Bacillus subtilis* by Single–Stranded Plasmid DNA," *Journal of Bacteriology*, vol. 165, No. 3, pp. 1015–1018 (1986).

Schulga, A. et al, "An approach to construction of Hybrid Polypeptide molecules–homologue recombination method," *Nucleic Acids Research*, vol. 22, No. 18, pp. 3808–3810 (1994).

Shao, Z. et al, "Random–priming in vitro recombination: an effective tool for directed evolution," *Nucleic Acids Research*, vol. 26, No. 2, pp. 681–683 (1998).

Shi, X.–B. et al, "Rapid PCR Construction of a Gene Containing Lym–1 Antibody Variable Regions," *PCR Methods and Applications*, pp. 46–53 (1993).

Stemmer, William P.C., "DNA shuffling by random fragmentation and reassembly: in vitro recombination for molecular evolution," *Proc. Natl. Acad. Sci. USA*, vol. 91, pp. 10747–10751 (1994).

Stemmer, William P.C., "Searching Sequence Space: Using recombination to search more efficiently and thoroughly instead of making bigger combinatorial libraries," *Bio/Technology*, vol. 13, pp. 549–553 (1995).

Tawfik, D. et al, "Man–made cell–like compartments for molecular evolution," *Nature Biotechnology*, vol. 16, pp. 652–656 (1998).

Young, Michael, "The Mechanism of Insertion of a Segment of Heterologous DNA into the Chromosome of *Bacillus subtilis*," *Journal of General Microbiology*, 129, pp. 1497–1512 (1983).

Zhang, J.–H. et al, "Directed evolution of a fucosidase from a galatosidase by DNA shuffling and screening," *Proc. Natl. Acad. Sci. USA*, vol. 94, pp. 4504–4509 (1997).

Zhao, H. et al, "Optimization of DNA shuffling for high fidelity recombination," *Nucleic Acids Research*, vol. 25, No. 6, pp. 1307–1308 (1997).

Zhao, H. et al, "Molecular evolution by Staggered extension process (StEP) in vitro recombination," *Nature Biotechnology*, vol. 16, pp. 258–261 (1998).

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: peptide substrate
<221> NAME/KEY: VARIANT
<222> LOCATION: (1)...(1)
<223> OTHER INFORMATION: Xaa = Suc
<221> NAME/KEY: VARIANT
<222> LOCATION: (4)...(4)
<223> OTHER INFORMATION: Xaa = AMC (Suc-Ala-Phe-7-amino-4-methyl
      Coumarin)

<400> SEQUENCE: 1

Xaa Ala Phe Xaa
 1

<210> SEQ ID NO 2
<211> LENGTH: 6
<212> TYPE: PRT
<213> ORGANISM: Artificial Sequence
<220> FEATURE:
<223> OTHER INFORMATION: peptide substrate
<221> NAME/KEY: VARIANT
<222> LOCATION: (1)...(1)
<223> OTHER INFORMATION: Xaa = Suc
<221> NAME/KEY: VARIANT
<222> LOCATION: (6)...(6)
<223> OTHER INFORMATION: Xaa = pNA (Suc-Ala-Ala-Pro-Phe-
      paranitroanalide)

<400> SEQUENCE: 2

Xaa Ala Ala Pro Phe Xaa
 1               5
```

SCREENING UNDER NUTRIENT LIMITED CONDITIONS

FIELD OF THE INVENTION

This invention is directed to methods for obtaining populations of cells in culture having similar density. It is also directed to methods of screening populations of cells for a phenotype of interest, including improved production of products and production of improved products.

BACKGROUND OF THE INVENTION

Microorganisms are being widely used as sources of useful chemical products, whether naturally occurring or through genetic engineering. Screening of organisms, particularly single cell organisms, is necessary for identifying those that produce useful products or useful products in more abundant quantities. Such identified organisms may then be isolated and utilized for their useful attributes.

Traditionally, screening of a population of organisms has been performed on agar plates. The population is usually spread on plates containing an indicator for a target enzyme, for example a chromogenic substrate, or skim milk to detect proteases. Colonies of the plated organism which produce elevated levels of the target enzyme can be detected, based on the intensity of color, the clearing zone, etc.

The method of screening by plating on agar plates has several disadvantages. The conditions on agar plates are very different from production conditions, which generally involve high-density fermentation. Therefore, a strain of an organism which produces elevated levels of a product on agar will not necessarily do so during production. Furthermore, the intensity of a reporting signal on an agar plate is dependent on the size of a given colony, masking variations in productivity between strains. Agar plate screens usually favor fast-growing strains which tend to give stronger signals.

The analysis of microcolonies has recently been described (Yang et al., Gene 173:19–23 (1996)). This method allows screening of large numbers of colonies on a single agar plate. However, this method still suffers from the problems mentioned above.

More recently, screening of populations of organisms has been performed on microtiter plates. This method generally involves distributing individual clones into wells of microtiter plates, for example by using a colony picker. The cells are then grown in a rich medium which mimics production conditions, allowing cells to grow to a high density. The cells are allowed to grow for various lengths of time. Samples are withdrawn for analysis, frequently requiring dilution of the sample to bring the activity of the target enzyme into the range of the detection method. Activity can be measured by various means, e.g., using chromogenic or fluorogenic substrates, radioactivity, etc.

The microtiter screening methods described above have several disadvantages. They require several liquid handling steps, which limits the throughput and/or requires robotics, which is very expensive. Liquid handling steps are also sources of error. It is also difficult to provide cultures in microtiter plates with oxygen, which is essential for many hosts. Furthermore, the cultures grow to a high density, resulting in changing medium conditions, such as pH, nutrient concentrations, by-products, etc. The changing medium conditions affect the productivity of the cells, resulting in the identification of strains which produce well under such conditions, but not necessarily under production fermentation conditions.

Therefore, there is a need for a rapid and efficient and cost-effective means for screening large numbers of cells for individual strains having preferred productivity of a product under conditions that closely approximate production fermentation conditions. Such a screen would be useful for identifying not only cells of a population with naturally occurring preferred properties, but also for identifying such preferred members of a population resulting from induced mutagenesis.

SUMMARY OF THE INVENTION

The present invention provides novel methods for obtaining a plurality of populations of cells having similar density and screening cell populations for a phenotype of interest, including improved production of products and production of improved products. In one aspect, the method comprises culturing a plurality of samples from an initial population of cells, in a medium containing at least one nutrient in limiting concentration. Growth of cells in each sample is controlled by the limiting nutrient to produce subpopulations having a similar cell density. This greatly simplifies the comparison of the subpopulations. In one embodiment, the cells are from a single initial population which may be a single organism type or cell line or a pool of preferred cells. The samples may be inoculated at various cell densities by various methods. Different limiting nutrients may be used, and the samples may be cultured in various receptacles.

In addition, the present invention provides methods for screening a population of cells of interest for cells having a phenotype of interest. The method comprises obtaining from the cell population of interest a plurality of subpopulations of cells of similar density by culturing samples of the cell population of interest. The samples comprise cells from the population of interest and a cell culture medium containing a limiting nutrient that controls cell growth such that cells in each sample grow to a similar density. Subpopulations comprising cells having the phenotype of interest are then identified.

In another embodiment, the invention provides methods of screening a population of cells of interest for cells having the phenotype of improved production of one or more products of interest. This method comprises the steps of obtaining from the cell population of interest a plurality of subpopulations of cells of similar density by culturing samples of the cell population of interest. The samples comprise cells from the population of interest and a cell culture medium containing a limiting nutrient that controls cell growth such that cells in each sample grow to a similar density. The amount of the product produced by the individual subpopulations is then measured. In a preferred embodiment, the improved production is during stationary phase. In a preferred embodiment, improved production is increased total production or increased production over time. Preferably, the amount of the product is measured. In one embodiment, measuring is by measuring activity of the product in each of the plurality of cell populations. In a preferred embodiment, the samples contain or have added to them a substance that detects the presence of each of the products. In one preferred embodiment, the substance is a substrate of the product. In another preferred embodiment, the substance is a ligand of the product. Preferably, the substance is fluorogenic or chromogenic.

Also provided by the invention is a method of screening a cell population of interest for cells having the phenotype of producing an improved product of interest. In one aspect, the improved product has increased activity over an unimproved product. The method comprises obtaining a plurality of subpopulations from the population of interest by culturing samples from the population of interest with at least one limiting nutrient which controls cell growth. In a preferred embodiment, the activity of the product is measured in the subpopulations to determine the relative activity of the product made by each.

In addition, the invention provides a method of screening a cell population of interest for cells having the phenotype of producing a product of interest having altered selectivity of substrate(s). The method comprises obtaining a plurality of subpopulations from the population of interest by culturing samples from the population of interest with at least one limiting nutrient which controls cell growth. The samples contain or have added to them, together or sequentially, two or more different substrates for the product of interest. In a preferred embodiment, the activity of the product on each substrate is measured in the subpopulations. Preferably the substrates are fluorogenic, are distinguishable from each other and are independently measurable.

Also provided is a method of screening a cell population of interest for cells having the phenotype of producing a product of interest having increased stability. The method comprises obtaining a plurality of subpopulations from the population of interest by culturing samples from the population of interest with at least one limiting nutrient which controls cell growth. In a preferred embodiment, the amount of product present over time or activity of the product over time is measured under non-optimal conditions for a product of interest not having increased stability. The non-optimal conditions may include temperature, pH, concentration of solutes, presence of proteases, presence of detergents and presence of solvents. Preferably, the measuring is done at more than one time point.

In another aspect, the invention provides a method of screening a cell population of interest for cells having the phenotype of improved efficiency of production of a product of interest. The method comprises obtaining a plurality of subpopulations from the population of interest by culturing samples from the population of interest with at least two limiting nutrients. One of the limiting nutrients controls cell growth while the other(s) is necessary for the production of the product of interest. The amount of the product produced in each of the subpopulations is measured to determine the efficiency of production of the product. In a preferred embodiment, the second and subsequent limiting nutrients are carbon and/or nitrogen.

The invention also provides a method of screening a cell population of interest for cells having the phenotype of improved production of a product of interest. The method comprises obtaining a plurality of subpopulations from the population of interest by culturing samples from the population of interest with at least two limiting nutrients. A first limiting nutrient limits the growth of the cells of each sample, while the at least second limiting nutrient is a substrate for the product of interest that, when reacted with the product, provides the same nutrient as the first. Samples having cells which produce more of the product of interest will reach a greater cell density. Cell density of the subpopulations is measured, wherein higher cell density shows higher production of the product of interest. In a preferred embodiment, cell density is measured by optical density. In another embodiment, cell density is measured by relative fluorescence for a fluorescent product produced by the cells of the population of interest.

Further provided herein is a method according to any of the screening methods described above, further comprising subjecting the cell population of interest to random mutagenesis or recombination. In a preferred embodiment, the cell population of interest is subjected to a mutagenic substance. In another embodiment, the steps of the method are subsequently repeated on preferred cell populations identified in previous screenings.

DETAILED DESCRIPTION OF THE INVENTION

The present invention is directed to methods of screening a population of cells. In one aspect, the method provides for obtaining a plurality of subpopulations of cells of similar density, derived from an initial population and representative of individual members of that initial population. The populations are grown in a medium which contains one nutrient in limited quantity, which allows one to control the cell density of the subpopulations. Such a collection of cell subpopulations is useful to screen for members of the initial population having preferred characteristics, particularly the ability to produce improved amounts of or an improved version of a product of interest.

The invention has many advantages over previously known cell culture systems. Most known screening assays favor fast-growing cells. The invention controls cell density through one or more limiting nutrients. Slow-growing cells will take longer to deplete the limiting nutrient, but they will ultimately reach cell densities similar to the fast-growing cells. This improves the chance of identifying mutations which have adverse effects on cell growth but lead to increased productivity or improved product properties. Preferably, the invention also avoids any $O_2$ limitation, precluding the need for shaking and allowing for the use of high density formats, such as bundles of capillaries, which allow limited oxygen transfer.

Generally, the subpopulations are of similar density, allowing for direct comparison of products, for example, enzymes produced. Aspects of the production of these products, including quantity produced, activity of the product, and the product's utilization of different substrates, can be compared under conditions that match large-scale fermentation conditions. As the cell density in each sample can be controlled by the concentration of the limiting nutrient, one can minimize changes in the culture medium that are caused by the metabolic activity of the cells. Thus, the conditions under which the cells are cultured throughout the cultivation closely resemble the conditions at the beginning of the cultivation. The culturing conditions, such as cell density and culture media components, can also be easily modified to optimize the desired characteristic, which modifications will be readily translated to large-scale production applications. The screening methods of the invention are also performed on cells in the stationary phase, further resembling large-scale fermentation conditions.

The methods of the invention provide for screening a population of cells having a diverse genetic make-up to identify individual cells in the population having phenotypes of interest. These methods allow for screening of cell populations having genetic diversity induced by external manipulation, such as through mutagenesis of the population. The methods are useful for screening large numbers of cells, and lend easily to high-throughput screening applications.

In general, the method involves producing a plurality of samples from a population of cells of interest and growing the cells of these samples to produce a plurality of subpopulations. The cell suspension medium contains at least one nutrient in limiting concentration so that the maximum cell density to which each subpopulation can grow is controlled, producing subpopulations of similar density. The resultant cell density is determined by the concentration of the limiting nutrient, rather than the growth rate of the various strains in the population.

The phrase "of interest" is used herein to designate a group, composition, trait, etc. that is under consideration and identified or identifiable.

In a preferred embodiment, the samples are taken from a cell suspension of an initial population of cells. By "initial population of cells", "initial cell population" and grammatical equivalents thereof is meant a population of cells from which one or more cells is subsequently grown into at least one subpopulation of cells. By "population of cells", "cell population", "population" and grammatical equivalents thereof herein is meant a mixture of 5 to $10^{15}$ cells which are genetically diverse. By "subpopulation" is meant a population of cells grown from one or more cells taken from an initial population.

In the invention, the cells may be any kind capable of growth under cell culture conditions. Cell types useful in the method include, but are not limited to yeast, bacteria, archaebacteria, fungi, including filamentous fungi, plant cells, and animal cells, including insect and mammalian cells. Preferred cell types include Bacillus and *E. coli*.

The initial population of cells can be from any source, provided that they can be grown in cell culture. In a preferred embodiment, the initial population from which the cell suspension samples are taken is of a single cell type.

In the methods herein, cells are grown in culture. By "growing cells in cell culture", "culturing cells" and grammatical equivalents thereof is meant providing cells in a cell culture medium having at least the minimum nutrients to support growth and viability of the cells in/on a receptacle under conditions that promote cell growth and viability, including any combination of nutrients, salts, buffers and other components recognized as beneficial to the specific cells to be cultured. As will be appreciated by those skilled in the art, the composition of the cell culture medium, as well as the conditions under which the cells are cultured, can vary and will largely depend on the type of cell to be cultured. Methods for culturing cells are well known in the art. In a preferred embodiment, temperature and humidity of the cultures are controlled to limit evaporation and condensation. Modification of cell culture medium composition and culture conditions to optimize cell growth and viability for a given application is common practice and well within the skill of the ordinary artisan. Further direction regarding culturing cells is provided in the Examples below.

In a preferred embodiment, the cells are cultured in receptacles which provide for culturing a large number of individual cell culture samples. Preferred receptacles for use in the present invention include, but are not limited to, plates which contain multiple depressions which can hold culture medium (multi-well plates), ultra high density plates, plates with through holes, CD-like disks, coherent capillary arrays, bundles of capillaries or vesicles, microfabricated channels and sprayed droplets of liquid and combinations thereof. Most preferably, multi-well plates having as many as 96, 384, 1536 or more wells are used. Multiple receptacles can be used simultaneously.

In the methods of the invention, a plurality of samples is taken from an initial population of cells. By "sample of an initial population of cells", "sample of a population of interest", "sample" and grammatical equivalents thereof is meant a volume of cell culture medium containing a subset of an initial population of cells.

In a preferred embodiment, samples of the initial population of cells are introduced to the receptacle and the cells therein are grown to produce subpopulations of cells derived from the initial cell population. Inoculation of the samples may be done prior to, simultaneously with or after introduction of medium to the receptacle. By "inoculation" is meant the distributing of cells from the initial population into the samples. Inoculation may be performed by several methods known in the art. In a preferred embodiment, inoculation is performed by random dilution of a suspension of the population of cells, followed by introduction of volumes of the suspension to the receptacle. In another embodiment, inoculation is achieved by colony picking. In still another embodiment, individual cells from the initial population are isolated, for example by a cell sorter, and introduced to the samples. Preferably, the samples are distinct and identifiable within the receptacle, for example one sample per well of a multi-well plate.

In a preferred embodiment, the samples are of similar volume. By "similar volume" is meant herein that when a measurement of activity of a product made by a population of cells in a sample is made, such as the measurement of a fluorescent product from a fluorogenic substrate by an enzyme produced by the cells, the measurement would not be significantly different between samples having identical cells grown in them under identical conditions.

In a preferred embodiment, the samples of the initial cell population have a low inoculation density. By "low inoculation density" is meant herein a density such that the majority of samples taken randomly from the suspension will have three cells or less, preferably two, and more preferably only one cell. Preferably, the samples average less than 1.4 cells each. More preferably, the samples average 0.5 cells each. As will be appreciated by those in the art, the desired cell density of the samples can be obtained by adjusting the dilution of a suspension of the initial cell population.

In another embodiment, the inoculation density of the samples is from 5 to 5000 cells per sample.

After the samples have been prepared, the cells in each sample grow to a cell density that is mainly dependent on the concentration of a limiting nutrient. If a sample is inoculated with one or a few cells, then the resulting subpopulation will be highly clonal, i.e., with the exception of a few spontaneous mutants, all cells in the subpopulation will be genetically identical to the cells that were initially placed in that sample. This situation is beneficial if the differences in phenotype between the cells in the initial population are close to the detection limit of the assay used. One has the best chance of identifying a cell with a phenotype of interest if the entire subpopulation in the sample is genetically identical to that cell. This is of particular importance if cells with the phenotype of interest grow slower than the average cell of the initial population.

In a preferred embodiment, a cell sorter (or other device) is used to distribute individual cells into the receptacles. This enables one to control the inoculation density of the samples. In a preferred embodiment, each sample is inoculated with one cell.

In another preferred embodiment, cells growing on solid medium are transferred into individual samples. This ensures that most samples contain cells from one clone only, which facilitates the identification of cells which differ only slightly from the average of the population. The transfer of cells into the receptacles can be performed manually or using a robotic work station. Most of the methods used to transfer cells from solid medium into receptacles allow limited control of the number of cells that get transferred. It is an advantage of the invention that the final cell density in the subpopulations is determined by the concentration of a limiting nutrient and not by the inoculation density.

In another preferred embodiment, the inoculation density is higher than one cell per samples, e.g., 3–1000 cells per sample. In this case, each subpopulation will represent a mixture of different clones. This approach is preferable if one is screening for cells which differ significantly in their phenotype from the average of the population. As a result, one is able to identify a subpopulation which contains a desirable clone, even if that clone only represents a fraction of the cells in the subpopulation. Working with a higher inoculation density enables one to screen a large initial population with a limited number of receptacles.

In the methods of the invention, the samples of the initial population of cells contain at least one limiting nutrient. By "limiting nutrient", "nutrient in limiting concentration" and grammatical equivalents thereof is meant a nutrient in the medium that is depleted as a result of growth of the cells before any other nutrient in the medium. A preferred limiting nutrient is phosphate. Other preferred limiting nutrients include potassium, magnesium, nitrogen carbon, sulphur, and trace elements. Still other preferred limiting nutrients include amino acids, growth factors, vitamins and other specific requirements for the growth of the particular population of cells of interest. However, the skilled artisan will appreciate that many components of the cell medium, and combinations thereof, can act as a limiting nutrient. The limiting nutrient may be in elemental form, or may be in any molecular form whereby it may be utilized by a cell as a nutrient. For example, suitable sources of carbon included sugars, polysaccharides, alcohols and other organic molecules that may be metabolized by a cell. Selection of an appropriate limiting nutrient is within the ordinary skills of an artisan in the field.

In a preferred embodiment, the limiting nutrient is in the medium that is used to make the samples of the initial population of cells. As will be appreciated by those of skill in the art, the limiting nutrient may be introduced to the cells at any time, as long as the limiting nutrient is present in the cell culture medium during the culturing of the cell(s) in the samples.

In a preferred embodiment, the cells stop growing once the limiting nutrient has been depleted from the sample, resulting in subpopulations of cells whose density is primarily dependent on the amount of a limiting nutrient and not on the growth rate of the cell(s) or the inoculation density of the original sample. Preferably, the cells enter stationary phase after the limiting nutrient is depleted and the cells stop growing and remain productive.

Accordingly, the invention provides methods for obtaining a plurality of subpopulations of cells. By "plurality" is meant more than one. However, the skilled artisan understands that as many as $10^9$ or more subpopulations can be obtained by the methods discussed herein.

In a preferred embodiment using the method above, the plurality of subpopulations of cells have a similar density and size (i.e., number of cells), due to the presence of a limiting nutrient in the culture medium and the similar volume of each sample, respectively. By "similar density" herein is meant a number of cells per volume such that when a measurement of activity of a product made by a population of cells in a sample is made, such as the measurement of a fluorescent product from a fluorogenic substrate by an enzyme produced by the cells, the measurement would not be significantly different between samples having identical volumes of identical cells.

The method for obtaining a plurality of populations of cells described above finds use in a number of applications, particularly for screening an initial population of cells for cells having a phenotype of interest. By "phenotype" is meant any detectable trait of a cell. Preferred phenotypes include, but are not limited to, improved production of one or more products of interest, improved efficiency in producing a product of interest and production of an improved product of interest. Improved products of interest include, but are not limited to, products having improved activity, altered selectivity for substrates and increased stability.

Other preferred phenotypes include the ability to grow and/or produce a product of interest under conditions in which the average cell of the initial population cannot. Such conditions include those wherein a nutrient is in a form such that it can only be utilized by cells having an altered phenotype from the average and those wherein the pH, temperature, and/or presence of toxins, solutes and/or solvents hinder growth and/or viability of average cells of the initial population.

In methods for screening a population of cells of interest for a phenotype of interest, a plurality of subpopulations of cells is obtained from the population of interest as described above. Subpopulations having a phenotype of interest are then identified. It will be apparent to those of skill in the art that the specific means for identifying a phenotype of interest will be determined by the particular phenotype to be identified. Assays for a variety of cell phenotypes are well known in the art and determination of a particular assay is well within the skill of the ordinary artisan.

In one aspect of the invention, a method of screening a population of cells of interest for cells having improved production of one or more products of interest is provided. By "improved production" herein is meant a total production amount or a production rate that is altered and preferred over production of the product by cells not having improved production. In one embodiment, production is greater than the average of the population. In another embodiment, production is less than the average of the population. In a preferred embodiment, individual cells produce greater amounts of one or more products and less amounts of one or more others.

By "product of interest" and grammatical equivalents thereof is meant any product of the physiological/biochemical activity of the cells of the population of interest, including, but not limited to, polypeptides, nucleic acids and carbohydrates and metabolites thereof. Preferably, the product of interest is a polypeptide, more preferably an enzyme.

In a preferred embodiment, the product of interest is selected from the group consisting of lipase, cellulase, endo-glucosidase H, protease, carbohydrase, reductase, oxidase, isomerase, transferase, kinase, phosphatase, alpha-amylase, glucoamylase, lignocellulose hemicellulase, pectinase and ligninase. In another embodiment, the product of interest is a therapeutic selected from the group consisting of vaccines, cytokines, receptors, antibodies, hormones, and factors including growth factors.

In a preferred embodiment, the product is a protease. In one aspect, the protease is FN4. Other preferred products include proteases homologous to subtilisin, phytases, cellulases and esterases. Sequences of Genbank accession numbers are incorporated herein by reference. Genbank is known in the art, see, e.g., Benson, D A, et al., Nucleic Acids Research 26:1–7 (1998) and http://www.ncbi.nlm.nih.gov/.

As the skilled artisan will appreciate, the products may be endogenous or heterologous. An endogenous product is one produced by the innate genetic make-up of the cell, including naturally occurring mutations and allelic variations of native products. "Heterologous", as used herein, means the product is produced by recombinant means or otherwise a product of induced mutagenesis. Therefore, the product may be native to the cell, but is produced, for example, by transformation with a self replicating vector containing the nucleic acid encoding the product of interest. Alternatively, recombinant could be wherein one or more extra copies of a native nucleic acid sequence are integrated into the genome by recombinant techniques. Furthermore, the recombinant product could be made as a result of a mutation of the cell's genome induced by a mutagenic agent, as further described below.

A phenotype of interest could be affected by numerous endogenous and heterologous genes. These include cells having increased metabolic efficiency and cells which produce fewer side products, as further described below.

In a preferred embodiment, the limiting nutrient(s) is/are not directly required for the production of the product of interest. For example, cell growth can be limited by limiting the concentration of the carbon source; however, a carbon source may be required for the production of the product by the cells, therefore limiting production upon depletion of the limiting nutrient. Preferred limiting nutrients are listed above.

The method further comprises measuring the amount of the product of interest in each of the plurality of subpopulations, from which the relative production of the product of interest in individual cells of the population of interest is derived. As will be appreciated by the skilled artisan, a number of means of measuring a product of a cell population can be used, depending largely on the product to be measured. For example, molecules with specific affinity for the product of interest, such as antibodies, may be used to label or precipitate the product of interest.

In a preferred embodiment, the samples contain or have added to them a substance that can detect the product of interest. When the product of interest is an enzyme, preferably the suspension contains a substrate of the enzyme, more preferably a substrate that is fluorogenic or chromogenic. By "fluorogenic substrate" and grammatical equivalents thereof is meant a substance or molecule with which the product of interest specifically interacts, whereby the fluorescent characteristics of the substrate change in a detectable way. In a preferred embodiment, fluorescence of the substrate changes following interaction with the product of interest, more preferably the change is quantifiable, for example by measuring luminescence. Likewise, a "chromogenic substrate" means a substance or molecule whose optical characteristics changes in a detectable way following interaction with the product of interest. Preferably, the change in the chromogenic substrate is quantifiable, for example by measuring density. This way, the activity of the enzyme product of interest is measured.

In a preferred embodiment, the substance that can detect a product of interest is a ligand of the product of interest. More preferably, the substance is a low molecular weight ligand. In a preferred embodiment, the ligand has a fluorescent marker. In a preferred embodiment, the amount of the product of interest is measured using the method of fluorescence polarization. Femades, P. B., *Curr. Opin. Chem. Biol.* 2(5):597–603 (1998).

In another preferred embodiment, the samples contain or have added to them more than one substance that can detect a product of interest. The additional substance(s) can detect the same product or a different product. For example, the suspension can contain a second fluorogenic substrate that reacts with the product of interest to produce a fluorescent signal. Preferably, each substance(s) is distinguishable from the others so that each may be measured independently. For example, the signal of an additional fluorogenic substrate(s) can have different fluorescent stimulation and/or emission wavelengths from the first, allowing for the enzymatic activity on the different substrates to be differentiated. Alternatively, cell populations selected for a desired product activity can be tested for activity with the additional substrate(s) in a subsequent assay. This enables the identification of cells with altered specificities or cells which produce various products in altered ratios.

As will be appreciated by those of skill in the art, the controlled density of the plurality of cell subpopulations, dictated by the concentration of limiting nutrient, allows for direct comparison between the different subpopulations. For example, a difference in measured enzyme activity between subpopulations translates directly either to a difference in the amount of the product produced by the cells of each subpopulation or a difference in the enzymatic activity of the products produced in each subpopulation. In a preferred embodiment, each subpopulation is grown from approximately one cell; therefore, usually each cell in a given population will be a clone, having the same genetic make-up and product production characteristics. In addition, since the limiting nutrient keeps the cell subpopulations from growing to high density, the product density is also controlled, allowing measurement of the product activity that might not be measurable without dilution of populations grown under non-limited growth conditions.

In a preferred embodiment, measurement of the activity of the enzyme product of interest indicates the relative amount of the product in each subpopulation. As discussed above, the plurality of subpopulations of cells of the present invention have a similar cell density. Therefore, in this embodiment, comparison of the activity of the enzyme product of interest can be made between each of the plurality of subpopulations of cells, from which the relative amount of enzyme produced in each can be determined. Furthermore, the change in the amount of detectable substrate over time can be used to determine the relative amount of the enzyme produced over time. As will be appreciated by those in the art, the relative amount of a product of interest between samples can be confirmed by subsequent analysis, such as an ELISA specific for the product, HPLC, mass spectrometry or electrophoresis.

In another aspect of the invention, methods are provided for screening a population of cells of interest for cells that produce an improved product of interest in an individual cell of the population. By "improved product", "improved product of interest" and grammatical equivalents thereof herein is meant a product of one or more cells of the population of interest having a desired characteristic not found in the majority of the cells of the population, which can be any alteration, increase or decrease. In a preferred embodiment, the improved product of interest has increased activity, more preferably increased enzymatic activity. In another aspect, the improved product has, alternatively or in addition, a different specific activity, preferably an altered substrate specificity, from the majority of cells of the population of interest. Other characteristics which may be considered an improvement are increased stability, changes in optimum pH or temperature, increased resistance to proteolysis and improved secretability.

In this aspect of the invention, a plurality of subpopulations of cells is obtained from a suspension of the population of cells of interest, as described above. As described above, in one embodiment the cell density of the suspension is adjusted so that the samples have a low inoculation density. The samples are also of similar volume. Furthermore, in a preferred embodiment, the relative activity of an enzyme product of interest between the plurality of subpopulations of cells is determined as described above.

In a preferred embodiment, measurement of the activity of the enzyme product of interest in each of the plurality of subpopulations indicates the relative activity of the individual product in each of the plurality of samples, whereby individual cells of the population of cells of interest that produce an improved enzyme product are identified.

In a preferred embodiment, the methods provide for screening a population of cells of interest for cells having improved efficiency of production of a product of interest. By "efficiency of production" is meant that the ratio of product produced per amount of raw material used from the culture medium is increased. In this embodiment, the samples contain at least two limiting nutrients, a first limiting nutrient which controls the growth of the subpopulation and other limiting nutrients that limit the ability of the cell to produce the product of interest. In a preferred embodiment, the limiting nutrient that limits the production of the product of interest is carbon or nitrogen. In this embodiment, increased production of the product of interest indicates increased efficiency of production.

In a preferred embodiment of the invention for each of the screening methods described above, the population of cells of interest is subjected to random mutagenesis or recombination prior to obtaining the plurality of samples. Methods of random mutagenesis and recombination are well known in the art. Exemplary methods are found in Miller, J. H., *A Short Course in Bacterial Genetics,* Cold Spring Harbor Laboratory Press, New York (1992).

Further instruction in mutagenesis techniques is found in the examples below. In a preferred embodiment, mutagenesis procedures are done prior to suspension of the initial population.

In a preferred embodiment, a population of cells are treated with a mutagenic agent. Many such agents are available commercially and are well known to the skilled artisan. A preferred mutagenic agent is ethyl methanesufonate (EMS). Following the mutation/recombination procedure, the cells are suspended in culture medium and the methods described above are followed.

In a preferred embodiment, cells are subjected to successive rounds of mutation and growth as described herein. In this embodiment, one or more subpopulations having desired characteristics are selected and isolated. In a preferred embodiment, if more than one subpopulation is selected, they are pooled. The selected population is then subjected to mutagenesis/recombination, suspended and cultured as described in the methods above. As will be appreciated by those of skill in the art, mutation and screening may be repeated as many times as desired. By this method, cells having still more desirable characteristics can be obtained.

In a preferred embodiment, a template device is used to facilitate identification and retrieval of subpopulations from the plurality of cell subpopulations which have desired characteristics. Preferably, generation of the template is automated, as data from individual subpopulations is measured and those having desirable characteristics are identified. Preferably, the template is physically brought into alignment with the receptacle containing the subpopulations, those subpopulations having desired characteristics being noticeably identified. For example, as fluorescence data from individual subpopulations in a multi-well plate are measured, a spread sheet is generated with the data and the wells having the preferred fluorescence output (usually the highest) are identified. A picking template, such as a 1:1 scale image of the multi-well plate showing the location of each well, is then generated such that the wells containing the subpopulations having the desired characteristics are marked. Overlaying the multi-well plate on the template allows for simple identification of the desired populations.

It will be apparent to those of skill in the art that the methods of the present invention are easily applied to a high-throughput screening paradigm. By "high-throughput screening paradigm", "high-throughput screening" and grammatical equivalents thereof is meant any system design to detect individuals having an identifying signal or trait from a large group. High-throughput screening is a common and expanding practice in the art (de Silva et al., *PNAS, USA* 96(15):8336–8337 (1999); Sandman et al., *Chem. Biochem.* 6(8):541–551 (1999); Zlokarnik et al., *Science* 279(5347):84–88 (1998)). Generally, a plurality of assays are performed simultaneously in high throughput screens.

Preferably, cells of subpopulations identified as having a phenotype of interest are isolated. Any number of cells of the identified subpopulation can be isolated, for example by removing a volume of the sample in which the subpopulation was grown. The isolated cells may then be grown under any conditions that promote the cells' viability. In one embodiment, the cells are reintroduced into the assay as an initial population or a component thereof, as described above. In another embodiment, the isolated cells are grown in cell culture medium having a composition that is modified from the sample, whereby optimum conditions for production of the product of interest are identified. In still another embodiment, the isolated cells are grown under large scale fermentation conditions in medium having the same composition and limiting nutrient as the sample, or a composition providing an optimized environment for the production of the product of interest, as just described.

Variations of the invention described herein will be apparent to those of ordinary skill in the art. It is understood by those of skill in the art that the steps of the methods described herein can vary. It is also understood, however, that while various options (of components, properties selected or order or repetition of steps) are provided herein, the options are also each provided individually, and can each be individually segregated from the other options provided herein. Moreover, steps which are obvious and known in the art that will increase the effectiveness of any of the steps described herein are intended to be within the scope of the invention. For example, the skilled artisan may apply various fluorescence or chromogenicity measuring techniques, cell culture variations, background reduction techniques, etc. All references cited herein are expressly incorporated by reference in their entirety.

The following examples serve to more fully describe the manner of using the above-described invention, as well as set forth best modes contemplated for carrying out various aspects of the invention. It is understood that these examples in no way serve to limit the true scope of this invention, but rather are presented for illustrative purposes.

EXAMPLES

Example 1
Isolation of Bacillus Strains which Produce Increased Amount of the Protease FN4

Screening Protocol

Unless otherwise indicated, reagents were purchased from Sigma (Saint Louis, Mo.). Culture medium consisted of a minimal MOPS medium with 40 mM glucose, 10 ppm soytone, 5 ug/ml chloramphenicol, and 5 $\mu$M phosphate.

EMS mutagenesis involved treatment of 1ml early log phase OS6.31 cells (OD 0.2) with 1% EMS for 20 minutes at 37° C. and 280 RPM, followed by two 1 ml medium washes, and 5 hours outgrowth in 4 ml medium at 37° C. and 280 RPM. 15% glycerol stocks were prepared and their CFU determined by plating serial dilutions on L-agar plates.

The following steps were used to fill the 1536-well plates with mutagenized cells. A 1536-well plate (#782101, Greiner Labortechnik, Frickenhausen, Germany) was placed, inverted, into a tray containing a mixture of medium, 43 EMS treated cells/ml, and 7.5 $\mu$M Suc-Ala-Phe-AMC (Suc-Ala-Phe-7-amino-4-methyl Coumarin; (SEQ ID NO: 1) AMC-084, Enzyme System Products, Livermore Calif.) (suspension). The trays were designed to hold 4 plates and are stackable, therefore several trays were prepared at once. The trays were placed into a vacuum chamber and the chamber was evacuated to 69 mm Hg, at which point the vacuum was released, the plates removed from the trays, and individual plate lids (#656161, Greiner Labortechnik, Frickenhausen, Germany) applied. Approximately equal volumes of suspension is obtained in each well, due to the uniform volume of the wells. Twenty 1536-well plates were prepared, and placed into a humidified incubator box at 37° C. without shaking.

The resulting 1536-well plates consisted of wells with or without cells, at a ratio that depended on the cell plating density. The target plating density was 60% empty wells (0.5 cells/well). The plates were incubated until 10 to 20% of substrate was hydrolyzed by the bulk of the wells containing cells, typically 48 h. Hydrolysis was measured using an excitation of 360 nm and an emission of 465 nm in 1536-well compatible fluorescent plate reader (HTS 7000 Plus, Perkin Elmer, Norwalk, Conn.).

The raw fluorescent data was transferred to a spreadsheet (Excel, Microsoft, Redmond, Wash.), where the data for each plate could be summarized and a "picking" template printed (HP LaserJet 5Msi, HP, Palo Alto, Calif.). The picking template assisted in rapid isolation of cells from the top fluorescent wells. The more protease secreted, the greater the fluorescence. The template consisted of a 1:1 scale image of a 1536-well plate on which selected individual well images were darkened. The darkened wells corresponded to the highest fluorescence wells of the 1536-well plate. After aligning a plate on top of this image, the top fluorescence wells appeared darkened when viewed from above. The darkened wells guided the insertion of a pipette tip, which removed 5 ul of culture.

The culture was transferred to a well of a 96-well plate containing 100 ul of 100 mM Tris 8.6 and 0.005% TWEEN-80. After the five highest fluorescence wells of each 1536-well plate were aliquot into individual wells, 100 ul of 2 mg/ml Suc-Ala-Ala-Pro-Phe-pNA (Suc-Ala-Ala-Pro-Phe-paranitroanalide; (SEQ ID NO: 2) PNA-85, Enzyme System Products, Livermore, Calif.), 100 mM Tris 8.6 and 0.005% TWEEN-80 was added to each well of the 96-well plate. The rate for paranitroanalide formation was measured by following the increase in 410 nm absorbance in a 96-well plate reader (Spectra Max 250, Molecular Devices, Sunnyvale, Calif.). The rate measurement facilitated isolation of top producing wells by reducing the noise of the primary screen, and confirming enzyme specificity.

The cultures with the highest rate from the screen are pooled and cycled into another round of EMS and screening.

TABLE 1

Rate of AMC hydrolysis following successive rounds directed evolution.

| Round[1] | Population[2] | Screen[3] | Selected[4] | Rate[5] |
|---|---|---|---|---|
| 1 | NL5P | 1,800 | 3 | 8 ± 1.6 |
| 2 | NL6P | 18,000 | 3 | 18 ± 2.4 |
| 3 | NL9P | 14,000 | 17 | 30 ± 5.0 |
| 4 | NL13P | 9,000 | 20 | 34 ± 5.5 |
| 5 | NL15P | 19,000 | 20 | 35 ± 5.6 |

[1]successive round of EMS mutagenesis
[2]name of EMS library
[3]number of EMS treated cells screened
[4]number of cells passed onto next screening round
[5]rate of sAAF-AMC hydrolysis: fluorescence divided by screening time

Example 2
Isolation of a Mutant with Increased Specific Activity

The gene coding for the protease FN4 and its signal and propeptide were mutagenized. The same screen as described in Example 1 was used. A variant was isolated which had 50% specific activity on the substrate Suc-AAPF-pNA, which was used for the secondary screen.

Example 3
Isolation of Mutant which Produces Increased Amounts of a Compound of Interest A production cell strain is subjected to random mutagenesis to generate an initial population of mutants. The cells are suspended in a medium containing limiting concentrations of phosphate. In addition, the medium contains a low molecular weight ligand that is fluorescent and binds to a compound of interest produced by the cells. The suspension is distributed into 1536-well plates and incubated. At one or more time points after the cultures reach stationary phase, the fluorescence polarization is measured. The ligand in the medium binds to the produced compound of interest which leads to an altered fluorescence polarization. Mutants which produced increased amounts of the compound of interest can be identified based on the measured polarization signal.

Example 4
Isolation of a Mutant which Produces an Increased Amount of Phytase A phytase producing cell strain is subjected to random mutagenesis to generate an initial population of mutants. The cells are suspended in medium containing limiting concentrations of phosphate and phytate. The suspension is distributed into 1536-well plates and incubated. Cells which produce increased amounts of phytase are able to utilize the phytate in the culture medium as a source of phosphate and at an increased rate. Such subpopulations can be identified based on their increased optical density. To enhance detection, a gene encoding a fluorescent product (such as green fluorescent protein from Aequoria victoria) is cloned into the cells and measure the density of a subpopulation based on fluorescence.

What is claimed is:

1. A method for obtaining a plurality of subpopulations of cells having a similar density comprising culturing a plurality of samples from an initial population of cells, wherein said samples contain at least one limiting nutrient whereby the maximum cell density to which the cells can grow is controlled, such that a plurality of populations of cells having a similar density is obtained.

2. The method of claim 1, wherein the cells of said initial population are from a single population of cells.

3. The method of claim 1, wherein said initial population is a population of pooled cells.

4. The method of claim 1, wherein said samples are taken randomly from a cell suspension.

5. The method of claim 1, wherein the inoculation density of said samples is less than 1.4 cells per sample.

6. The method of claim 1, wherein each of said samples initially comprises 3 or less cells, and wherein a substantial number of said samples comprise at least one cell.

7. The method of claim 1, wherein each of said samples initially comprises 5–5000 cells.

8. The method of claim 1, wherein inoculation of said samples is by random dilution.

9. The method of claim 1, wherein inoculation of said samples is by colony picking.

10. The method of claim 1, wherein inoculation of said samples is by placement of individually isolated cells into each of said samples.

11. The method of claim 1, wherein each of said at least one limiting nutrient is/are selected from the group consisting of phosphate, magnesium, nitrogen, carbon and sulfur.

12. The method of claim 1, wherein said culturing is in a receptacle or form selected from the group consisting of one or more multi-well plates, ultra-high density plates, capillary arrays, bundles of capillaries, microfabricated channels, plates with through-holes, vesicles, CD-like disks and sprayed droplets.

13. The method of claim 2, wherein said initial population of cells is a population of a single type of organism.

14. The method of claim 2, wherein said initial population of cells is from a cell line.

15. The method of claim 7, wherein said inoculation density is less than 0.5 cells per sample.

16. A method of screening a population of cells of interest for cells having a phenotype of interest, said method comprising:
   a) obtaining from said population of cells of interest a plurality of subpopulations of cells having a similar density by culturing a plurality of samples from said population of cells of interest, wherein said samples contain at least one limiting nutrient whereby the maximum cell density to which the cells can grow is controlled; and
   b) identifying subpopulations of said plurality of subpopulations having a phenotype of interest.

17. A method of screening a population of cells of interest for cells having a phenotype of interest, wherein said phenotype is improved production of one or more products of interest, said method comprising:
  a) obtaining from said population of cells of interest a plurality of subpopulations of cells having a similar density by culturing a plurality of samples from said population of cells of interest, wherein said samples contain at least one limiting nutrient whereby the maximum cell density to which the cells can grow is controlled; and
  b) measuring the amount of each of said products of interest produced in each of said plurality of subpopulations of cells, whereby cells of said population of cells of interest having improved production of said product(s) are identified.

18. The method of claim 17, wherein said improved production is during stationary phase.

19. The method of claim 17, wherein said improved production is increased total production or increased production over time.

20. The method of claim 17, wherein said improved production is decreased total production or decreased production over time.

21. The method of claim 17, wherein said improved production is increased production of a first product of interest and/or decreased production of other products of interest.

22. The method of claim 17, wherein said one or more products of interest is/are each selected from the group consisting of an enzyme, a non-enzyme protein, an enzyme product, a nucleic acid, and a carbohydrate.

23. The method of claim 17, wherein said measuring is by measuring the amount of activity of said product in each of said plurality of populations of cells.

24. The method of claim 17, wherein said samples contain or have added to them one or more substances that detect(s) the presence of said one or more products of interest.

25. The method of claim 17, wherein at least one of said at least one limiting nutrient is not required for the production of said product.

26. The method of claim 17, wherein said measuring is done at more than one time point.

27. The method of claim 21, wherein said other products of interest are selected from the group consisting of parallel products of metabolic precursors of said first product of interest, proteases, and proteins other than said first product of interest.

28. The method of claim 24, wherein at least one of said one or more substances is/are a substrate for each of said one or more products of interest.

29. The method of claim 24, wherein at least one of said one or more substances is/are a ligand for each of said one or more products of interest.

30. The method of any one of claims 24, 28 and 29, wherein said one or more substances is/are fluorogenic and/or chromogenic.

31. The method of claim 30, wherein said measuring is by measuring luminescence.

32. The method of claim 30, wherein said measuring is by the method of fluorescence polarization.

33. The method of claim 30, wherein said measuring is by densitometry.

34. A method of screening a population of cells of interest for cells having a phenotype of interest, wherein said phenotype is production of a product of interest having improved activity, said method comprising:
  (a) obtaining a plurality of subpopulations of cells from said population of cells of interest having a similar density by culturing a plurality of samples from said population of cells of interest, wherein said samples contain at least one limiting nutrient whereby the maximum cell density to which the cells can grow is controlled; and
  (b) measuring the activity of said product produced in each of said subpopulations of cells, whereby the relative activity of said product produced by cells of said population of cells of interest is determined.

35. The method of claim 34, wherein said improved product of interest has increased activity over an unimproved product of interest.

36. The method of claim 34, wherein said samples contain or have added to them one or more substances that detect(s) the presence of said product.

37. The method of claim 36, wherein said one or more substances is/are a substrate for said product.

38. The method of claim 37, wherein said samples contain or have added to them more than one substrate for said product.

39. A method of screening a population of cells of interest for cells having a phenotype of interest, wherein said phenotype is production of a product of interest in individual cells of the population having altered selectivity for substrates of said product, said method comprising:
  (a) obtaining a plurality of subpopulations of cells from said population of cells of interest having a similar density by culturing a plurality of samples from said population of cells of interest, wherein said samples contain at least one limiting nutrient whereby the maximum cell density to which the cells can grow is controlled, and wherein said samples contain or have added to them, together or sequentially, two or more different substrates for said product of interest; and
  (b) measuring the activity of said product on each of said substrates in each of said subpopulations of cells, whereby altered selectivity for substrates of the product of interest produced in individual cells of said population of cells of interest is determined.

40. The method of claim 39, wherein said two or more different substrates are fluorogenic.

41. The method of claim 40, wherein said fluorogenic substrates are distinguishable from each other and independently measurable.

42. A method of screening a population of cells of interest for cells having a phenotype of interest, wherein said phenotype is production of a product of interest having increased stability, said method comprising:
  (a) obtaining from said population of cells of interest a plurality of subpopulations of cells having a similar density by culturing a plurality of samples from said population of cells of interest, wherein said samples contain at least one limiting nutrient whereby the maximum cell density to which the cells can grow is controlled; and
  (b) measuring the amount or activity of said product produced in each of said subpopulations of cells under one or more non-optimal conditions for the stability of a non-improved product of interest, whereby the stability of said product produced by individual cells of said population of cells of interest is determined.

43. The method of claim 42, wherein said conditions are selected from the group consisting of temperature, pH, concentration of one or more solutes, presence of one or more proteases, presence of one or more detergents, and presence of one or more solvents.

44. The method of claim 42, wherein said measuring is done at more than one time point.

45. A method of screening a population of cells of interest for cells having a phenotype of interest, wherein said phenotype is improved efficiency of production of a product of interest, said method comprising:
(a) obtaining from said population of cells of interest a plurality of subpopulations of cells having a similar density by culturing a plurality of samples from said population of cells of interest, wherein said samples contain at least two limiting nutrients whereby the maximum cell density to which the cells can grow is controlled by a first limiting nutrient and all other limiting nutrients limit the ability of said subpopulations to produce said product; and
(b) measuring the amount of said product produced in each of said plurality of populations of cells, whereby the relative production of said product by cells of said population of cells of interest is determined.

46. The method of claim 45, wherein said other limiting nutrient(s) is selected from the group consisting of carbon and nitrogen.

47. The method of claim 45, wherein said measuring is by measuring activity of said product of interest.

48. A method of screening a population of cells of interest for cells having a phenotype of interest, wherein said phenotype is improved production of a product of interest, said method comprising:
a) obtaining from said population of cells of interest a plurality of subpopulations of cells by culturing a plurality of samples from said population of cells of interest, wherein said samples contain a first limiting nutrient which controls cell growth and at least a second limiting nutrient which is the same as said first limiting nutrient but in a form such that it is a substrate for said product of interest and not available as a nutrient unless reacted with said product of interest; and
b) measuring the cell density of each of said subpopulations, whereby higher cell density shows greater production of said product of interest.

49. The method of claim 48, wherein said measuring is by measuring optical density or fluorescence of a fluorescent product produced by said subpopulations.

50. The method of any one of claims 17, 34, 39, 42, 45 and 48, further comprising, prior to step (a), the step of:
subjecting said population of cells of interest to random mutagenesis or recombination.

51. The method of claim 50, wherein said subjecting is by exposure to a mutagenic agent.

52. The method of claim 51, wherein said mutagenic agent is EMS.

53. The method of claim 50, wherein the steps are subsequently repeated using one or more subpopulation identified in the previously obtained plurality of subpopulations as the cell population of interest.

54. The method of claim 53, wherein when more than one subpopulation is used from the previously obtained plurality of subpopulations, those subpopulations are pooled to make the population of interest for the subsequent screening.

55. The method of any one of claims 17, 34, 39, 42, 45 and 48, wherein said screening is performed in a high-throughput screening paradigm.

* * * * *